(12) United States Patent
Fu et al.

(10) Patent No.: US 8,637,649 B2
(45) Date of Patent: Jan. 28, 2014

(54) PROCESS FOR THE PREPARATION OF (2R,3S)-2-(HYDROXYMETHYL)-5-METHOXYTETRAHYDROFURAN-3-OL AND ACETYLATED DERIVATIVES THEREOF, FREE OF PYRANOSE COMPOUNDS

(75) Inventors: Xing Fu, Acton, MA (US); Albrecht Zumbrunn, Territet (CH)

(73) Assignee: Johnson Matthey Public Limited Co., London (GB)

( * ) Notice: Subject to any disclaimer, the term of this patent is extended or adjusted under 35 U.S.C. 154(b) by 0 days.

(21) Appl. No.: 13/303,710

(22) Filed: Nov. 23, 2011

(65) Prior Publication Data

US 2012/0238734 A1 Sep. 20, 2012

Related U.S. Application Data

(60) Provisional application No. 61/416,594, filed on Nov. 23, 2010.

(51) Int. Cl.
 *C07G 3/00* (2006.01)
 *C07H 17/00* (2006.01)
(52) U.S. Cl.
 USPC ........................................................ 536/18.6
(58) Field of Classification Search
 None
 See application file for complete search history.

(56) References Cited

FOREIGN PATENT DOCUMENTS

WO    WO-2010/129211 A2    11/2010

OTHER PUBLICATIONS

Trost, Comprehensive Organic Synthesis—Selectivity, Strategy and Efficiency in Modern Organic Chemistry, vols. 1-9, 1991, p. 594.*
Dermer, Proceedings of the Oklahoma Academy of Science, 32 (1951); p. 104.*
Ness et al., "2-Deoxy-D-ribose. VII. Crystalline 2-Deoxy-3,5-di-*O-p*-nitrobenzoyl-D-ribosyl Chloride and Related Derivatives," *The Journal of Organic Chemistry*, 1961, vol. 26, No. 8, pp. 2895-2899.
Deriaz et al., "Deoxy-sugars. Part VI. The Constitution of β-Methyl-2-deoxy-L-ribopyranoside and of αβ-Methyl-2-deoxy-L-ribofuranoside," *Journal of the Chemical Society*, 1949, pp. 2836-2841.
Ludek et al., "A greener enantioselective synthesis of the antiviral agent North-methanocarbathymidine (N-MCT) from 2-deoxy-D-ribose," *Tetrahedron*, 2009, vol. 65, No. 41, pp. 8461-8467.
Gold et al., "1,3,5-Tri-O-acetyl-2-deoxy-α, β-D-erythro-pentofuranose from 2-deoxy-D-erythro-pentose," *Nucleosides & Nucleotides*, 1990, vol. 9, No. 7, pp. 907-912.
Bhat, "2-Deoxy-3,5-di-*O-p*-toluoyl-D-*erythro*-pentosyl Chloride—Preparation of a Crystalline O-Acyl-2-deoxypentofuranosyl Halide," *Synthetic Procedures in Nucleic Acid Chemistry*, 1968, New York: Wiley, pp. 521 and 522.
International Search Report dated Apr. 3, 2012, from PCT International Application No. PCT/US2011/062038.

* cited by examiner

*Primary Examiner* — Layla Bland
(74) *Attorney, Agent, or Firm* — RatnerPrestia

(57) ABSTRACT

A method of preparing a ribofuranose derivative essentially free of pyranose compounds includes a step of contacting a solution of MDR containing MDRP as an impurity in a solvent including methanol and/or tetrahydrofuran with at least one alkali metal periodate under conditions sufficient to oxidize at least a portion of the MDRP. MDR containing at most 5 wt % of MDRP based on the total weight of MDR and MDRP may be produced.

18 Claims, No Drawings

PROCESS FOR THE PREPARATION OF (2R,3S)-2-(HYDROXYMETHYL)-5-METHOXYTETRAHYDROFURAN-3-OL AND ACETYLATED DERIVATIVES THEREOF, FREE OF PYRANOSE COMPOUNDS

CROSS-REFERENCE TO RELATED APPLICATIONS

This application claims priority of U.S. Provisional Patent Application No. 61/416,594, filed Nov. 23, 2010, the disclosure of which is incorporated herein by reference in its entirety for all purposes.

FIELD OF THE INVENTION

This invention pertains to a method for making a ribofuranose derivative, in particular methyl-2-deoxyriboside.

BACKGROUND OF THE INVENTION

The title compound, also referred to as methyl-2-deoxyriboside (MDR), is a ribofuranose derivative that has traditionally been prepared by acid-catalyzed methanolysis of 2-deoxy-D-ribose (2DR).

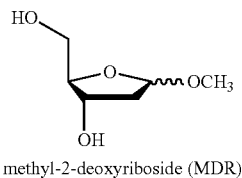

methyl-2-deoxyriboside (MDR)

MDR may be used as a starting material for the production of 2DR derivatives, useful as intermediates in many pharmaceutical synthesis applications.

During the formation of MDR, a significant amount of the pyranose isomer (3R,4S)-6-methoxytetrahydro-2H-pyran-3,4-diol, also referred to as methyl-2- deoxyribopyranoside (MDRP), is generated along with the desired product.

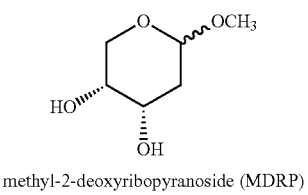

methyl-2-deoxyribopyranoside (MDRP)

MDRP generates pyranose impurities in derivatives prepared from the MDR, and therefore it is desirable to remove it prior to preparing such derivatives. For example, the use of sodium periodate to remove MDRP by oxidation is described by R. K. Ness et al., The Journey of Organic Chemistry, 1961, Vol. 26, No. 8, pp. 2895-2899. The oxidation is carried out in an aqueous medium that is buffered with phosphate to pH 6.4-6.8, apparently to protect the acid sensitive methoxy group at position 1. The complicated workup procedure involves the use of ion exchangers to remove periodate oxidation products. Simpler and more easily scalable methods of removing MDRP from MDR would therefore benefit the pharmaceutical industry.

SUMMARY OF THE INVENTION

In one aspect, the invention provides a method of preparing a ribofuranose derivative essentially free of pyranose compounds, including a step of contacting a solution of MDR containing MDRP as an impurity in a solvent including methanol and/or tetrahydrofuran with at least one alkali metal periodate under conditions sufficient to oxidize at least a portion of the MDRP.

In yet another aspect, the invention provides MDR containing at most 5 wt % of MDRP based on the total weight of MDR and MDRP.

DETAILED DESCRIPTION OF THE INVENTION

Now disclosed is a method of decreasing an amount of MDRP present as an impurity accompanying MDR by oxidizing the MDRP with an alkali metal periodate in a solvent comprising methanol and/or tetrahydrofuran. Unlike previous methods such as that of Ness et al., which require the use of a phosphate buffer in water during the oxidation, it has now been found that oxidation in a substantially methanol and/or tetrahydrofuran-based solvent can proceed very well without a buffer. The oxidation can be performed without any added phosphate, and in fact without any added buffer at all, and the reaction mixture may be essentially free of phosphate and/or any other buffer. Therefore, in some embodiments of the invention, the reaction mixture consists essentially of MDR, MDRP, at least one alkali metal periodate and a solvent comprising methanol and/or tetrahydrofuran and optionally water.

Avoiding the use of buffer greatly simplifies workup and isolation of the purified MDR, especially on a commercial scale. Typically, no metal salts other than one or more alkali metal periodates are added to the reaction mixture prior to or during the oxidation. Therefore, in some embodiments the reaction mixture is essentially free of metals not derived from the metal periodate(s). The alkali metal periodate will typically be the potassium and/or sodium salt.

The oxidation reaction may nonetheless be performed in the presence of metals not derived from the alkali metal periodate(s), but typically at least 50 mol % of all metals present during the oxidation come from the one or more alkali metal periodates. More typically, at least 60 mol %, or at least 70 mol %, or at least 80 mol %, or at least 90 mol %, or at least 95 mol % of the metals come from the periodate(s).

The natural pH of the reaction mixture is typically about 4, corresponding to unbuffered sodium periodate. However, the reaction can be performed at a pH of at least 2.5, or at least 3.0, or at least 3.5. The pH may be as high as 4.5, or 5.0, or 5.5.

The amount of periodate is typically based on the amount of MDRP accompanying the MDR, and this can be determined for example by gas chromatography (GC) analysis. The molar ratio of periodate to MDRP is typically at least 0.9:1 and more typically at least 1.0:1. In some embodiments, it is at least 1.1:1, or at least 1.2:1, or at least 1.3:1, or at least 1.4:1, or at least 1.5:1. The molar ratio has no particular upper limit, but may be constrained by issues relating to raw material cost and ease of reaction workup. The ratio will typically be at most 2.0:1, or at most 3.0:1, or at most 4.0:1, or at most 5.0:1.

The physical form of the periodate affects the rate of MDRP destruction. It has been found that finely powdered periodate provides faster reactivity than granular material. Any means of providing fine particle size is suitable for use according to the invention. For example, finely powdered periodate may be made by grinding or milling granular or larger crystalline material. Alternatively, it may be made by rapidly cooling a hot solution of periodate in a solvent in which it is only marginally soluble, or by adding a solution of periodate in a good or mediocre solvent to a poor solvent. An example of the latter method is disclosed in Example 3, where a hot aqueous solution is added to a methanol solution of MDR, resulting in formation of solid sodium periodate as a fine white dispersion.

The oxidation reaction solvent may comprise a major amount of methanol, which may for example constitute at least 70 wt % of the solvent, or at least 75 wt %, or at least 80 wt %, or at least 85 wt %, or at least 90 wt %, or at least 95 wt %. The solvent may be essentially only methanol. The presence of some amount of water has also now been found to help accelerate the oxidation reaction, and there is no particular limit as to the amount of water that can be present with the methanol for purposes of the invention. It has, however, been found that excessive amounts of water make workup more laborious and time-consuming, and so certain practical limits may be in order, depending on the details of the particular situation.

In some cases, enough water is already present in the mixture to significantly increase reaction rate. This situation may for example occur if the solution of MDR in methanol is the partially worked-up reaction mixture obtained from forming MDR by acid-catalyzed methanolysis of 2DR. The resulting water of reaction may cause the water content of the solvent to be at least about 1.7 wt % without separate addition of water. Lower amounts of water are also effective, and the water content may in some embodiments be at least 0.1 wt %, 0.2 wt %. 0.3 wt %, 0.4 wt %, 0.5 wt %, or 1 wt %. In some embodiments, the water content is at least 2 wt %, or at least 3 wt %, or at least 4 wt %. The upper limits on water content are imposed by the above-noted minimum contents of methanol.

In some embodiments of the invention, the oxidation solvent may comprise a major amount of tetrahydrofuran. This may replace some or all of the methanol as described in the preceding paragraph, and the percentages of methanol and water described herein relate equally to percentages of tetrahydrofuran and water, or to percentages of methanol/tetrahydrofuran mixtures in any proportion and water.

Purified MDR prepared according to the invention contains a significantly lower amount of MDRP than was present prior to the oxidation. The amount of MDRP in the purified MDR is less than 5 wt %, or less than 4 wt %, or less than 3 wt %, or less than 2 wt %, or less than 1 wt %. Typically, the amount of MDRP is at most 0.5 wt %, or at most 0.15 wt %. In some embodiments, at most 0.10 wt % of MDRP is present, or at most 0.07 wt %, or at most 0.05 wt %. As used herein, references to wt % or ppm of MDRP are relative to the total combined weight of MDR and MDRP, unless the context clearly indicates otherwise. These levels of MDRP can be reached in the oxidation reaction mixture as well as the final isolated MDR after appropriate workup.

In one embodiment, the oxidation takes place at a pH of about 4 (the pH of an unbuffered sodium periodate solution) without cleavage of the methoxy group at room temperature in about 6 to 24 hours in methanol in the presence of 0 to 10 wt % water. For example, a solution of 2DR in methanol (10 mL/g) is treated with a catalytic amount of hydrogen chloride (0.014 equivalents as a solution in ether) and stirred until the 2DR is consumed. The resulting solution is treated with an excess of sodium bicarbonate to neutralize the hydrogen chloride, stirred for 30 min and filtered. The filtrate is treated with sodium periodate in water (5% of total volume) either as a suspension or as a hot solution and the mixture is stirred at room temperature for 18 hours or longer. Sodium bicarbonate is then charged, stirring continued for another 30 min and the mixture is filtered and concentrated to an oil. This oil may be dissolved in a suitable solvent and filtered to remove salts. Material suitable for use in the production of derivatives is obtained by concentration of the filtrate. In an alternative method, the periodate oxidation of MDRP may be performed in tetrahydrofuran, using MDR product formed by the above-mentioned acid-catalyzed methanolysis of 2DR with subsequent removal of some or all of the methanol. The amount of tetrahydrofuran may be the same on a weight basis as the amount of methanol that can be used for the oxidation, but lesser or greater amounts may be used as well.

MDR free of the pyranose impurity MDRP may be elaborated into other ribofuranose derivatives useful as pharmaceutical intermediates, correspondingly free of pyranose impurities. For example, acetylation of MDR provides [(2R,3S)-3-acetoxy-5-methoxy-tetrahydrofuran-2-yl]methyl acetate, which can in turn be converted to (4S,5R)-5-(acetoxymethyl)tetrahydrofuran-2,4-diyl diacetate as shown below.

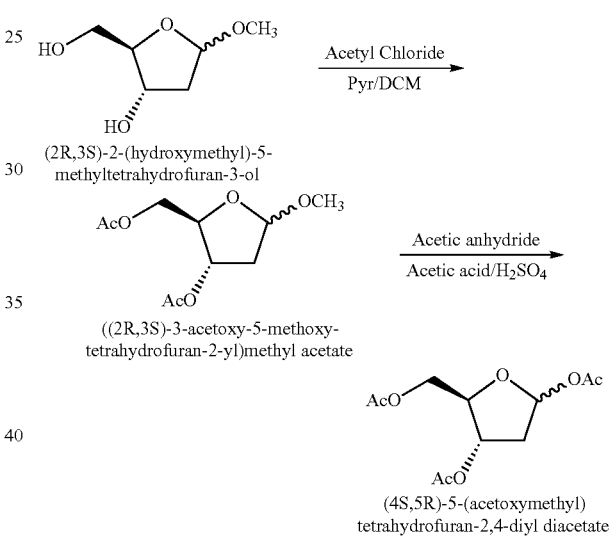

In the second step, acetolysis of [(2R,33)-3-acetoxy-5-methoxytetrahydrofuran-2-yl]methyl acetate using acetic anhydride in acetic acid as the solvent and catalyzed by sulfuric acid gives the corresponding tri-acetylated glycoside. The reaction is reported to be sensitive to a high concentration of sulfuric acid and high temperature, which result in charring and low product yields. In one traditional workup procedure, the reaction mixture is therefore poured into crushed ice and extracted with chloroform. While this procedure prevents charring and other product losses, it is problematic in that very stable emulsions are generated during the extraction steps due to the presence of large amounts of acetic acid, making phase separation difficult.

The current invention solves this problem by avoiding the addition of water in the workup. Instead, the catalytic amount of sulfuric acid in the reaction mixture is neutralized by adding an appropriate amount of solid sodium acetate to the mixture, thereby converting the sulfuric acid to sodium sulfate and forming additional acetic acid. This allows the mixture to then be heated to higher temperatures without decomposition of the product, and the solvent (acetic acid) can be removed by distillation. For example, this can be done under mild vacuum at 50° C. The product can be purified by thin film evaporation. This process is easy to scale up, and eliminates emulsion formation during workup.

EXAMPLES

Example 1

Formation of methyl-2-deoxyriboside and Destruction of methyl-2-deoxyribopyranoside by Oxidation 2-Deoxy-D-ribose (50 g, 0.373 mol) was charged into a 1 L 3-necked round bottom flask followed by methanol (500 mL). The mixture was stirred until dissolution. A solution of HCl in diethyl ether (5.0 mL, 0.005 mol) was added in one portion and the resulting mixture was stirred at room temperature overnight. Upon completion the batch was quenched by addition of solid sodium bicarbonate (7.0 g, 0.08 mol) and the resulting mixture was stirred for 30 min. The reaction mixture was filtered through a fritted funnel and the solid on the filter was washed with methanol. The wash filtrate was combined with the main product filtrate. The filtrate was transferred into a reaction flask via polyethylene tubing using vacuum. About 1.7 wt % of water of reaction was present at this point, relative to total solvent. Finely is powdered sodium periodate (12.0 g, 0.056 mol) was charged into the reaction flask in portions. The resulting suspension was stirred at room temperature for 6 h and then sampled for in-process GC testing. GC analysis indicated approximately 0.73% of MDRP in the reaction mixture.

The batch was continuously stirred at room temperature for additional 18 h and GC analysis was repeated. It indicated the presence of about 0.5% of MDRP in the reaction mixture. An additional solid sodium periodate (1.6 g, 0.007 mol) was charged and the resulting mixture was stirred at room temperature for 4 h. GC testing indicated no detectable MDRP in the reaction mixture. To quench the reaction, solid sodium bicarbonate (12.0 g, 0.149 mol) was charged to the reaction mixture and stirring was continued for another 15 min. The reaction mixture was filtered through a fritted funnel and the filtrate was concentrated in a rotary evaporator until no more condensate was observed. The resulting oil was diluted with acetonitrile (500 mL) and then filtered through a Celite pad. The filtrate was concentrated on a rotary evaporator to give the product (55.4 g, 106% yield).

Example 2

Formation of methyl-2-deoxyriboside and Destruction of methyl-2-deoxyribopyranoside by Oxidation A 22 L, 4-necked flask was set up in a secondary containment and equipped with overhead stirrer, temperature probe, nitrogen in/out adapter to an oil bubbler and a stopper on the fourth neck. 2-Deoxy-D-ribose (950 g, 7.08 mol) was charged to the reaction flask, followed by methanol (9.5 L, 235 mol). After the batch was fully dissolved, 1.0 M hydrogen chloride in diethyl ether (95 mL, 0.095 mol) was charged in one portion with an addition funnel. The ensuing endothermic reaction resulted in a temperature decrease to 9.6° C. The mixture was then stirred and allowed to slowly return to room temperature. The reaction was monitored by TLC (DCM/methanol 8:2) and GC (7.1% MDRP and trace amount of 2DR). Upon completion, solid sodium bicarbonate (190 g, 2.26 mol) was charged in one portion to quench the reaction, and the mixture was stirred for a minimum of 30 min. Slight gas evolution was observed during this time; no temperature change was observed. The mixture was filtered through a fritted funnel and the filtered solid was washed with methanol (250 mL). The wash filtrate was combined with the main product filtrate.

To the combined filtrates granular sodium periodate (154 g, 0.72 mol) was charged to the stirred solution in portions over a period of 30 min while monitoring the temperature. No exotherm was observed. The mixture was then stirred for 17 h at room temperature, followed by in-process GC analysis. The test result indicated that only a very small amount of MDRP had been destroyed. Water (533 mL) was added via addition funnel to the stirred solution over a period of 2 h. During this time the temperature of the mixture rose from 16.5° C. to 20.7° C. due to the exothermic oxidation reaction. Water constituted about 7.8 wt % of the solvent at this point. The mixture was then stirred at room temperature for 4.5 h. GC analysis indicated 1.42% of MDRP in the reaction mixture.

A second charge of granular sodium periodate (45.4 g, 0.21 mol) was added. After stirring the batch for another 7 h, the mixture (a white suspension) was reanalyzed (by GC) and the result indicated approximately 0.07% of MDRP in the batch. Solid sodium bicarbonate (120 g, 1.49 moles) was charged to the batch and stirring was continued for a minimum 30 min. The mixture was then filtered through a fritted funnel and the solid was washed with methanol (530 g, 700 mL). The filtrate was concentrated in a rotary evaporator to dryness. The concentrate was dissolved in acetonitrile (2 kg) and again evaporated until condensation ceased. The resulting oil was dissolved in acetonitrile (2 kg) and the solution was filtered to remove any solid. The filtrate was concentrated on a rotary evaporator at bath temperature of 30.±5° C. A third charge of acetonitrile (2 kg) was made and the mixture evaporated again and dried for 1 h under reduced pressure to give 1039 g of product.

Example 3

Formation of methyl-2-deoxyriboside and Destruction of methyl-2-deoxyribopyranoside by Oxidation A 50 L flask was set up in a secondary containment and equipped with overhead stirrer, temperature probe and nitrogen in/out adapter to an oil bubbler. 2-Deoxy-D-ribose (1500 g, 11.2 mol) was charged to the reaction flask, followed by methanol (11.9 kg). After the batch was fully dissolved, 1.0 M hydrogen chloride in diethyl ether (114 g) was charged in one portion with an addition funnel. The reaction was monitored by TLC (DCM/methanol 8:2) and GC (6.9° A) of MDRP and no 2DR) analysis. Solid sodium bicarbonate (184 g) was charged in one portion and the stirring continued for a minimum of 30 min. The mixture was filtered through a fritted funnel and the filtered solid was washed with methanol (0.6 kg). The wash filtrate was combined with the main product filtrate.

To the combined filtrates in the reaction flask was charged a hot solution of sodium periodate (312 g) in water (700 mL) at 63° C. in portions at a rate that maintained the batch temperature at ≤25° C. Upon addition of the aqueous periodate, the mixture became milky white, indicating the precipitation of finely dispersed solid periodate. The resulting mixture, in which water constituted about 6.7 wt % of the solvent, was stirred at about 23° C. for 2 h and then the GC analysis was repeated. GC analysis indicated 0.19% of MDRP in the reaction mixture.

Additional granular sodium periodate (24.2 g) was charged as a solid. After stirring for 11 h the mixture was reanalyzed and the analysis indicated 0.05% of MDRP in the batch. Solid sodium bicarbonate (302 g) was charged to the batch (white suspension) and stirring continued for another 30 min. The mixture was filtered through a fritted funnel and the filtered solid was washed with methanol (200 g). The filtrate was then concentrated under reduced pressure. Acetonitrile (3.0 kg×2) was charged to the concentrate, and then it was evaporated until condensation ceased. The resulting oil was dissolved in acetonitrile (3.0 kg) and the solution was filtered to remove any solid. The wash filtrate was combined with the main product filtrate, and the combined filtrate was concentrated on a rotary evaporator and dried for 1 h to give of the product (1.6 kg).

Comparative Example 4

Formation of methyl-2-deoxyriboside and Destruction of methyl-2-deoxyribopyranoside by Oxidation A 22 L, 4-necked flask was set up in a secondary containment and equipped with overhead stirrer, temperature probe, nitrogen in/out adapter to an oil bubbler and a stopper on the fourth neck. 2-Deoxy-D-ribose (948 g, 7.07 mol) was charged to the flask, followed by methanol (9.5 L, 235 mol). After the batch was fully dissolved, 1.0 M hydrogen chloride in diethyl ether (95 mL, 0.095 mol) was charged in one portion with an addition funnel. The ensuing endothermic reaction resulted in a temperature decrease, and the mixture was then stirred while its temperature slowly returned to room temperature (15° C.). The reaction was monitored by TLC (DCM/methanol 8:2), with later confirmation of content by GC. Upon completion, solid sodium bicarbonate (150 g, 1.71 mol) was charged in one portion and the stirring continued for another 40 min. The mixture was filtered through a fritted funnel and the filtered solid was washed with methanol. The wash filtrate was combined with the main product filtrate.

The reaction flask was cleaned and the combined filtrates were charged back into the flask. Granular sodium periodate (340 g) was charged to the stirred solution in portions over a period of 1 h while monitoring the temperature. No exotherm was observed. The mixture was then stirred for 18 h at room temperature, resulting in a white suspension. Solid sodium bicarbonate (190 g, 2.26 mol) was charged to the batch and stirring was continued for another 20 min. The mixture was filtered through a fritted funnel and the filtered solid was washed with methanol. The filtrate was concentrated in a rotary evaporator, followed by addition of acetonitrile (2 kg) and further evaporation until condensation ceased. The resulting oil was dissolved in acetonitrile (2 kg) and the solution was filtered to remove any solid. The filtrate then was concentrated on a rotary evaporator at bath temperature 35° C. and dried for 1 h to give the product (1046 g). GC analysis indicated the presence of 6.0% of MDRP in the product.

TABLE 1

Relative percentages of MDR and MDRP[1]

| Example # | Composition before NaIO$_4$ charge | | Product Composition | |
|---|---|---|---|---|
| | % MDR | % MDRP | % MDR | % MDRP |
| 1 | 94.1 | 5.9 | 100.0 | ND[2] |
| 2 | 92.7 | 7.3 | 99.9 | 0.11 |
| 3 | 92.8 | 7.2 | 99.9 | 0.08 |
| Comp. 4 | 93.2 | 6.8 | 94.0 | 6.00 |

[1]Both MDR and MDRP are a mixture of α and β anomers.
[2]None detected at a detection limit of 100 ppm MDRP in MDR.

Example 5

Synthesis of [(2R,3S)-3-acetoxy-5-methoxy-tetrahydrofuran-2-yl]methyl acetate

A 1039 g portion of MDR was charged to a 20 L 3-necked flask fitted with an overhead stirrer, a Claisen adapter with nitrogen in/out adapter to an oil bubbler, a temperature probe and a 1 L addition funnel. Anhydrous dichloromethane (5.5 kg, 4.15 L) was charged to dissolve the starting material in the reaction flask. Anhydrous pyridine (1203 g, 15.21 mol) was then charged in one portion with agitation, resulting in a temperature rise from 15.8° C. to 21.0° C. The mixture was then cooled to below −30° C. by means of an acetonitrile/CO$_2$ bath.

Acetyl chloride (1216 g, 15.49 mol) was charged to the addition funnel and added dropwise to the cooled mixture at <0° C. This addition took ~45 min. Thirty minutes after the end of the addition the cooling bath was removed and the mixture was stirred for 7 h while warming to room temperature. A sample was analyzed by TLC (ethyl acetate/heptane 1:1 and methanol/dichloromethane 2:8, PMA).

When the starting material was no longer detected, the flask was immersed in an ice/water bath and cooled to 6.6° C., and water (2.75 kg) was charged from the addition funnel over a period of 6 min, resulting in a final temperature of 11.1° C. The mixture was transferred to a separatory funnel. The organic layer was separated and the water layer was extracted with dichloromethane (2×480 g). The combined extracts were washed with 1 N aqueous HCl (1.4 L), followed by half saturated brine (2×750 g). The extract was transferred to a round bottom flask fitted with an overhead stirrer and dried over sodium sulfate for 60 min under agitation. The solid was removed by filtration and the filtrate was concentrated on a rotary evaporator at a bath temperature 35° C. Dichloromethane (2×200 g) was used to rinse the flask and the sodium sulfate. The rinse was charged to the flask on the rotary evaporator and concentrated. The product was further dried for 1 h on the rotary evaporator. The product was a brownish liquid, yield: 1543 g (85%).

Example 6

Synthesis of (4S,5R)-5-(acetoxymethyl)tetrahydrofuran-2,4-diyl diacetate

A 20 L, 3-necked flask was set up in a secondary containment environment and equipped with an overhead stirrer, Claisen adapter with temperature probe and nitrogen in/out adapter to an oil bubbler and an addition funnel. Acetic acid (2683 g) and acetic anhydride (1915 g, 18.76 mol) were charged to the reaction flask and stirred in an ice/water bath until the temperature of the mixture was at ≤6° C. Meanwhile the starting material (1533 g, 6.6 mol) was dissolved in acetic acid (1606 g) in the rotary evaporator flask.

Sulfuric acid 95 to 98% (18.6 g, 0.19 mol) was weighed into a vial. When the mixture in the reaction flask had reached a temperature ≤6° C., the sulfuric acid was charged to the batch in small portions over a period of 10 min, keeping the temperature at ≤8° C. The solution of starting material was then transferred in portions to an amber bottle using vacuum and charged from the amber bottle to the addition funnel. The solution was added slowly to the reaction mixture while keeping the temperature at ≤8° C. An additional 197 g of acetic acid was used to rinse the rotary evaporator flask and amber bottle, and the rinses along with the remaining amount (1300 g) of acetic acid were charged to the stirred mixture.

The cold bath was removed and the mixture was allowed to return to room temperature with stirring and monitoring by TLC (ethyl acetate/heptane 3:7, PMA). After stirring approximately 5.5 h the reaction was completed, and the batch was quenched by addition of solid anhydrous sodium acetate (64.9 g, 0.79 mol). The mixture was stirred for 30 min until the sodium acetate was completely dissolved, followed by addition of activated charcoal (46 g) and 30 min further stirring. The mixture was then filtered through a pad of Celite (300 g). Acetic acid (500 mL) was used to wash the reaction flask and the Celite pad.

The filtrate was then transferred to an evaporation flask in portions and concentrated on a rotary evaporator at a bath temperature of 50° C. When all of the solvent had been removed and condensation was no longer observed, the traps were emptied and the residue was dried on the rotary evaporator for 1 h at a bath temperature of 50° C. Xylenes (1 kg) were charged to the flask and evaporated to dryness at 50° C., followed by dilution with xylenes (3 kg) and cooling to room temperature. A fluffy solid was filtered off through a fritted funnel. Xylenes (730 g) were used to wash the solids on the filter. The filtrate was charged back to the rotary evaporator and concentrated and dried to give the crude product as a dark brown oil, 1644 g (96% of the theoretical yield).

The crude product was then subjected to thin film evaporation in four passes:

Pass 1: Vacuum 900 mTorr, T=50° C., feed pump: 100 rpm, rotator: 193 rpm. Product was in the nonvolatile fraction.

Pass 2: Vacuum 750 mTorr, T=78° C., feed pump: 50 rpm, rotator: 218 rpm. Product was in the nonvolatile fraction.

Pass 3: Vacuum 250 mTorr, T=120° C., feed pump: 50 rpm, rotator: 257 rpm. Product was in the volatile fraction as well as the nonvolatile fraction. The volatile fraction was retained and the nonvolatile fraction was subjected to Pass 4.

Pass 4: Vacuum 250 mTorr, T=120° C., feed pump: 50 rpm, rotator: 257 rpm. Product was in the volatile fraction, and was combined with volatile fraction from Pass 3.

The combined product fractions yielded 1166.7 g (63.3%).

Although the invention is illustrated and described herein with reference to specific embodiments, the invention is not intended to be limited to the details shown. Rather, various modifications may be made in the details within the scope and range of equivalents of the claims without departing from the invention.

What is claimed:

1. A method of preparing a ribofuranose derivative essentially free of pyranose compounds, comprising a step of contacting a solution of MDR containing MDRP as an impurity in a solvent comprising methanol with at least one alkali metal periodate under conditions sufficient to oxidize at least a portion of the MDRP, wherein the solution has a pH in a range from 2.5 to 5.5 during the contacting.

2. The method of claim 1, wherein after said contacting the amount of MDRP present is at most 5 wt % based on the total weight of MDR and MDRP.

3. The method of claim 1, further comprising subsequently isolating purified MDR from the solution, wherein the isolated MDR contains at most 5 wt % of MDRP based on the total weight of MDR and MDRP.

4. The method of claim 1, wherein the solution does not comprise any added buffer.

5. The method of claim 1, wherein the solution does not comprise any added phosphate.

6. The method of claim 1, wherein at least 50 wt % of all alkali metals in the solution comes from the at least one alkali metal periodate.

7. The method of claim 1, wherein methanol constitutes at least 70 wt % of the solvent.

8. The method of claim 1, wherein water constitutes from 0.1 wt % to 30 wt % of the solvent.

9. The method of claim 1 further comprising, prior to said contacting, preparing the solution of the MDR containing the MDRP by a method comprising contacting 2DR with methanol in the presence of an acid under conditions sufficient to convert substantially all of the 2DR to MDR containing the MDRP as said impurity.

10. The method of claim 1, wherein the at least one alkali metal periodate comprises sodium periodate.

11. The method of claim 10, wherein the sodium periodate is prepared by a process that includes adding aqueous sodium periodate to methanol that may optionally also contain water and/or the MDR containing the MDRP, under conditions sufficient to cause at least a portion of the sodium periodate to precipitate as a particulate solid.

12. A method of preparing a ribofuranose derivative essentially free of pyranose compounds, comprising a step of contacting a solution of MDR containing MDRP as an impurity in a solvent comprising tetrahydrofuran with at least one alkali metal periodate under conditions sufficient to oxidize at least a portion of the MDRP, wherein the solution has a pH in a range from 2.5 to 5.5 during the contacting.

13. The method of claim 1, further comprising converting the MDR to (4S,5R)-5-(acetoxymethyl)tetrahydrofuran-2,4-diyl diacetate.

14. The method of claim 13, comprising the steps of converting the MDR to [(2R, 3S)-3-acetoxy-5-methoxy-tetrahydrofuran-2-yl]methyl acetate and converting the [(2R,3S)-3-acetoxy-5-methoxy-tetrahydrofuran-2-yl]methyl acetate to said (4S,5R)-5-(acetoxymethyl)tetrahydrofuran-2,4-diyl diacetate.

15. The method of claim 14, wherein the step of converting the [(2R,3S)-3-acetoxy-5-methoxy-tetrahydrofuran-2-yl] methyl acetate to said (4S,5R)-5-(acetoxymethyl)tetrahydrofuran-2,4-diyl diacetate comprises reaction of the [(2R,3S)-3-acetoxy-5-methoxy-tetrahydrofuran-2-yl]methyl acetate with acetic anhydride in acetic acid in the presence of a catalytic amount of sulfuric acid;

wherein the method further comprises after the reaction a step of adding sodium acetate to the reaction mixture in an amount sufficient to neutralize the sulfuric acid.

16. The method of claim 12, further comprising converting the MDR to (4S,5R)-5-(acetoxymethyl)tetrahydrofuran-2,4-diyl diacetate.

17. The method of claim 16, comprising the steps of converting the MDR to [(2R, 3S)-3-acetoxy-5-methoxy-tetrahydrofuran-2-yl]methyl acetate and converting the [(2R,3S)-3- acetoxy-5-methoxy-tetrahydrofuran-2-yl]methyl acetate to said (4S,5R)-5-(acetoxymethyl)tetrahydrofuran-2,4-diyl diacetate.

18. The method of claim 17, wherein the step of converting the [(2R,3S)-3-acetoxy-5-methoxy-tetrahydrofuran-2-yl] methyl acetate to said (4S,5R)-5-(acetoxymethyl)tetrahydrofuran-2,4-diyl diacetate comprises reaction of the [(2R,3S)-3-acetoxy-5-methoxy-tetrahydrofuran-2-yl]methyl acetate with acetic anhydride in acetic acid in the presence of a catalytic amount of sulfuric acid;
  wherein the method further comprises after the reaction a step of adding sodium acetate to the reaction mixture in an amount sufficient to neutralize the sulfuric acid.

\* \* \* \* \*